(12) United States Patent
Van Hes et al.

(10) Patent No.: US 6,391,896 B1
(45) Date of Patent: May 21, 2002

(54) 3-TETRAHYDROPYRIDIN-4-YL INDOLES FOR TREATMENT OF PSYCHOTIC DISORDERS

(75) Inventors: Roelof Van Hes; Johannes A. M. Van Der Heijden; Cornelis G. Kruse; Jacobus Tipker; Martinus T. M. Tulp; Gerben M. Visser; Bernard J. Van Vliet, all of Weesp (NL)

(73) Assignee: Duphar International Research BV, Weesp (NL)

( * ) Notice: Subject to any disclaimer, the term of this patent is extended or adjusted under 35 U.S.C. 154(b) by 0 days.

(21) Appl. No.: 09/807,408

(22) PCT Filed: Oct. 15, 1999

(86) PCT No.: PCT/EP99/07912

§ 371 Date: Jul. 3, 2001

§ 102(e) Date: Jul. 3, 2001

(87) PCT Pub. No.: WO00/23441

PCT Pub. Date: Apr. 27, 2000

(30) Foreign Application Priority Data

Oct. 16, 1998 (EP) .............................................. 98203499

(51) Int. Cl.⁷ .................. C07D 401/06; A61K 31/4439
(52) U.S. Cl. ..................................... 514/339; 546/277.1
(58) Field of Search ........................ 546/277.1; 514/339

(56) References Cited

U.S. PATENT DOCUMENTS 5,693,655 A    12/1997   Bottcher et al.

FOREIGN PATENT DOCUMENTS

| DE | 44 14 113 A1 | 10/1995 |
|----|----|----|
| EP | 0 722 941 A2 | 7/1996 |
| EP | 0 722 941 A3 | 4/2000 |
| WO | WO 98/28293 | 7/1998 |

OTHER PUBLICATIONS

CA 134:534, Van Hes, Roelof et al. "Pyridyinylindole derivatives for treating psychotic disorders". year 2000.*

* cited by examiner

Primary Examiner—Jane Fan
(74) Attorney, Agent, or Firm—Finnegan, Henderson, Farabow, Garrett & Dunner, L.L.P.

(57) ABSTRACT

The invention is related to the following compounds:

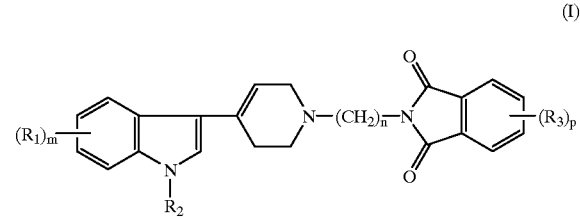

(I)

wherein all variables are as defined in the specification. The compounds are useful for treating psychotic disorders.

7 Claims, No Drawings

3-TETRAHYDROPYRIDIN-4-YL INDOLES FOR TREATMENT OF PSYCHOTIC DISORDERS

The invention relates to a novel group of 3-tetrahydropyridin4-yl indole derivatives of the formula (I):

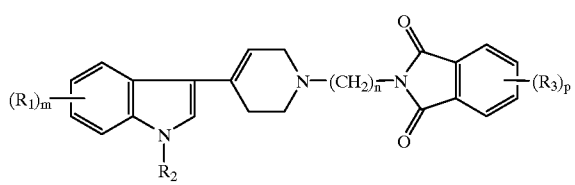

wherein:
- $R_1$ is halogen, $CF_3$, alkyl (1–3C), alkoxy (1–3C), CN or $SCH_3$
- m the value 0, 1 or 2
- $R_2$ is H or alkyl (1–3C)
- n has the value 3, 4, 5 or 6
- $R_3$ is halogen, alkyl (1–4C) or alkoxy (1–4C)
- p has the value 0, 1, or 2 and salts thereof.

It has been found that the compounds having formula (I) show high affinity for the dopamine $D_2$-receptor and are good serotonin reuptake inhibitors (SRI's).

Preferred compounds of the invention are compounds having formula (I) wherein $R_1$ hydrogen (i.e. m=0) or F, Cl, $CH_3$ or CN, and m=1, $R_2$ is H or $CH_3$, n=4, $R_3$ is hydrogen (i.e. p=0), or F or alkyl (1–4C), p=1, and the salts thereof. Especially preferred is the compound having formula (I) wherein $(R_1)m$ is F, $R_2$ is hydrogen, n=4 and p=0, and the salts thereof.

It has been found that the compounds according to the invention show high affinity for both the dopamine $D_2$ receptor and the serotonin reuptake site. This combination is useful for the treatment of schizophrenia and other psychotic disorders and might allow for a more complete treatment of all disease symptoms (e.g. positive symptoms and negative symptoms).

The compounds show activity as antagonists at dopamine $D_2$ receptors as they potentially antagonize apomorphine-induced climbing behavior mice. The compounds also show activity as inhibitors of serotonin reuptake, as they potentiate 5-HTP induced behaviour in mice.

The compounds are active in therapeutic models sensitive to clinically relevant antipsychotics (e.g. the conditioned avoidance response; Van der Heyden & Bradford, Behav. Brain Res., 1988, 31:61–67) and antidepressants or anxiolytics (e.g. suppression of stressinduced vocalization; van der Poel et al., Psychopharmacolgy, 1989, 97:147–148).

In contrast to clinically relevant dopamine $D_2$ receptor antagonists the described compounds have a low propensity to induce catalepsy in rodents and as such are likely to induce less extrapyramidal side effects than existing antipsychotics agents.

The inhibitory activity of serotonin reuptake inherent in these compounds may be responsible for the therapeutic effects observed in behavioural models sensitive to either antidepressants or anxiolytics.

The compounds can be used for the treatment of affections or diseases of the central nervous system caused by disturbances in either the dopaminergic or serotonergic systems, for example: aggression, anxiety disorders, autism, vertigo, depression, disturbances of cognition or memory and in particular schizophrenia and other psychotic disorders.

Pharmacologically acceptable acids with which the compounds of the invention can form suitable acid addition salts are for example hydrochloric acid, sulphuric acid, phosphoric acid, nitric acid, and organic acids such as citric acid, fumaric acid, maleic acid, tartaric acid, acetic acid, benzoic acid, p-toluene sulphonic acid, methanesulphonic acid and naphthalene sulphonic acid.

The compounds are their acid addition salts can be brought into forms suitable for administration by means of suitable processes using auxiliary substances such as liquid and solid carrier materials.

The compounds having formula (I) can be obtained as follows: by reaction of a compound of formula (II)

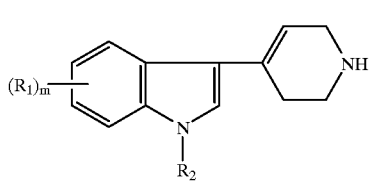

with a compound of the formula (III)

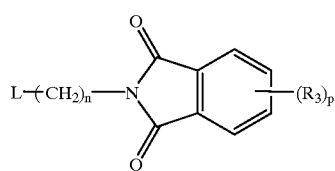

wherein the symbols have the above meanings and L is a so-called leaving group, for example bromo.

This reaction is carried out in a solvent such as acetonitrile in the presence of triethylamine or $K_2CO_3$ and Kl at reflux temperature, or a) by (i) reduction of the cyano group in a compound of formula (IV)

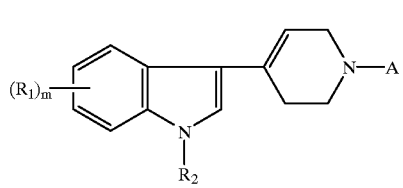

wherein A represents the group $-(CH_2)_{n-1}-CN$, to the corresponding group $-(CH_2)_n-NH_2$; and (ii) reacting the obtained amine with an optionally substituted phthalic anhydride of the formula (V)

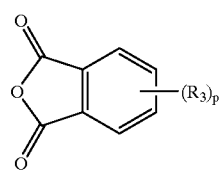

in which formula the symbols have the meanings give above.

Reaction step b (i) can be carried out for example with LiAlH$_4$ in an organic solvent such as tetrahydrofuran at reflux temperature.

Reaction step (ii) can be carried out for example in organic solvents such as tetrahydrofuran and toluene at reflux temperature.

The starting compounds as used in method a) of the formula (II) can be obtained in a manner known per se by reaching an optionally substituted indole derivate with 4-piperidone.

The starting compounds used in method b) having formula (IV) can be obtained by reaction of a compound having formula (II) with a bromoalkyl nitrite of the formula Br—(CH$_2$)$_{n-1}$—CN in a manner known per se.

The preparation of the compounds having formula (I) will now be described in more detail in the following Examples.

EXAMPLE 1

Preparation of 1-methyl-3-(1,2,3,6-tetrahydropyridin-4-yl)indole

To a solution of 4-piperidone. H$_2$O.HCl (50 g, 0.32 mol) in 100 ml of acetic acid and 150 ml of trifluoroacetic acid was added dropwise a solution of 1-methylindole (11.5 ml, 0.09 mol) in 100 ml of acetic acid at room temperature. After stirring for 1h the reaction mixture was concentrated (in vacuum, temp. ca. 30° C.), water was added, the mixture was made basic with potassium carbonate and extracted with ethyl acetate. The organic layer was separated, dried and purified by silica gel column chromatography (dichloromethane/methanol/ammonium hydroxide =84/15/1) to give 9 g (47%) of the title compound.

EXAMPLE 2

Preparation of 5-fluoro-3-(1,2,3,6-tetrahydropyridin-4-yl)indole

To a solution of sodium (60 g, 2.6 mol) in 1000 ml of methanol was added 5-fluoroindole (49 g, 0.36 mol) and 4-piperidone.H$_2$O.HCl (170 g, 1.11 mol). The mixture was heated under reflux for 18 h, then concentrated, water was added and extracted with ethyl acetate. The combined organic layer was dried over sodium sulfate and then concentrated. The resulting solid was dissolved in methanol (about 200 ml) and then diluted with water (about 1000–1500 ml). The precipitate was collected, washed with water and petroleum ether and then dried in a vacuum oven at 60° C. Yield 74 g (95%) of a yellow solid.

EXAMPLE 3

Preparation of N-[4-[4-[(5-fluoro-1H-indol-3-yl)-1,2,3,6-tetrahydropyridin-1-yl]butyl]-phthalimide.HCl (compound 1)

A solution of 5-fluoro-3-(1,2,3,6-tetrahydropyridin-4-yl) indole (7.5 g, 34.7 mmol), N-(4bromobutyl)phthalimide (10.8 g, 38.3 mmol), triethylamine (4.5 ml) and potassium iodide (5.5 g) in 150 ml of acetonitrile was heated under reflux for 18 h. The reaction mixture was concentrated and purified by silica gel column chromatografy (dichloromethane/methanol/ammonium hydroxide=92/7.5/0.5) to give 8.3 g of the title compound as a free base. Mp. 186° C. The hydrochloride was prepared by dissolving the above mentioned free base in 20 ml of 1M HCl in ethanol. The solution was concentrated and the resulting solid was washed with ether. Yield 8.4 g (54%) of compound 1, mp. 224° C. (dec.).

EXAMPLE 4

Preparation of 5-fluoro-3-[1-(3-cyanopropyl-1,2,3,6-tetrahydropyridin-4-yl]indole A solution of 5-fluoro-3-(1,2,3,6-tetrahydropyridin-4-yl) indole (10 g, 46 mmol), 4-bromobutyronitrile(5.6 ml, 56 mmol) potassium carbonate (6.3 g) and potassium iodide (7.6 g) in 100 ml of acetonitrile was heated under reflux for 18 h. The mixture was filtered and the residue on the filter was washed with dichloromethane/methanol/ammonium hydroxide=84/15/1. The organic layer was concentrated to give 10.9 g (83%) of the title compound. M.p 152° C.

EXAMPLE 5

Preparation of 5-fluoro-3-[1-(4-aminobutyl)-1,2,3,6-tetrahydropyridin-4-yl]indole To a solution of 5-fluoro-3-[1-(3-cyanopropyl)-1,2,3,6-tetrahydropyridin-4-yl]indole (10 g, 35 mmol) in 300 ml of dry THF was added slowly LiAlH$_4$ (2.0 g ). The mixture was stirred and heated to reflux for 2 h. Then the reaction mixture was cooled and water (1.9 ml) in THF (10 ml) was added slowly, followed by 2N sodium hydroxide (1.9 ml). This mixture was heated to reflux for 0.25 h, filtered over hyflo and concentrated to give 8.76 g (88%) of the title compound.

EXAMPLE 6

Preparation of N-[4-[4-(5-fluoro-1H-indol-3-yl)-1,2,3,6-tetrahydropyridin-1-yl]butyl]-4-fluorophthalimide (compound 19)

To a solution of 5-fluoro-3-[1-(4-aminobutyl)-1,2,3,6tetrahydropyridin-4-yl]indole (1.46 g, 5 mmol) in 20 ml of THF was added 4-fluorophthalic anhydride and 50 ml of toluene. The THF was removed by distillation and the resulting mixture was heated to reflux for 18 h, with azeotropic removal of water (Dean and Stark apparatus). The reaction mixture was concentrated and purified by silica gel column chromatografy (dichloromethane/methanol/ammonium hydroxide=92/7.5/0.5) to give 1.52 g (69%) of the title compound 19. M.p. 197–199° C.

According to method a) as illustrated in Examples 1–3, or method b) as illustrated in Examples 4–6 the compounds listed in the following Table have been prepared:

TABLE

| Comp. No | (R$_1$)$_m$ | R$_2$ | n | (R$_3$)$_p$ | Salt/base | Melt. point ° C. |
|---|---|---|---|---|---|---|
| 1 | 5-F | H | 4 | H | HCl | 224 (decomp.) |
| 2 | H | H | 4 | H | base | 193–4 |
| 3 | H | H | 3 | H | base | 190–2 |
| 4 | H | CH$_3$ | 4 | H | HCl | 230 |
| 5 | 7-CH$_3$ | H | 4 | H | base | 175–8 |
| 6 | 5-F | H | 3 | H | base | 174–6 |
| 7 | H | H | 4 | 3-F | base | 173–4 |
| 8 | H | H | 4 | 3-CH$_3$ | base | 184–5 |
| 9 | H | H | 4 | 4-CH$_3$ | base | 195–8 |
| 10 | 5-CN | H | 3 | H | base | amorph. |
| 11 | 5-CN | H | 4 | H | base | amorph. |
| 12 | 5-Cl | H | 4 | H | base | amorph. |
| 13 | H | H | 4 | 4-F | base | 197–8 |
| 14 | H | H | 4 | 4-t.C$_4$H$_9$ | fumarate | 243–5 |
| 15 | 5-F | H | 4 | 4-t.C$_4$H$_9$ | fumarate | 193–5 |
| 16 | 5-F | H | 4 | 3-CH$_3$ | base | 167–8 |
| 17 | 5-F | H | 4 | 4-CH$_3$ | base | 199–200 |
| 18 | 5-F | H | 4 | 3-F | base | 188–190 |
| 19 | 5-F | H | 4 | 4-F | base | 197–9 |
| 20 | H | H | 6 | H | base | 196–7 |
| 21 | 5-F | H | 6 | H | base | 170–2 |
| 22 | 5-F | H | 4 | 4,5-diCl | base | 216–8 |
| 23 | H | H | 4 | 4,5-diCl | base | 217–8 |
| 24 | 5-F | H | 5 | H | base | 194–8 |
| 25 | 5-F | H | 4 | 4-Cl | base | 186–8 |
| 26 | H | H | 4 | 4-Cl | base | 209–215 |

What is claimed is:

1. A compound having formula (I)

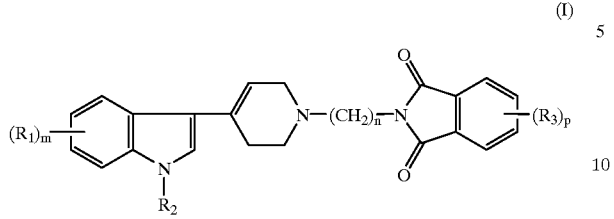

wherein $R_1$ is halogen, $CF_3$, $(C_1-C_3)$alkyl, $(C_1-C_3)$alkoxy, CN or $SCH_3$;

m has the value 0, 1 or 2;

$R_2$ is H or $(C_1-C_3)$alkyl;

n has the value 3, 4, 5 or 6;

$R_3$ is halogen, $(C_1-C_4)$alkyl, or $(C_1-C_4)$alkoxy;

p has the value 0, 1 or 2;

or a pharmacologically acceptable acid addition salt thereof.

2. A compound as claimed in claim 1, wherein $(R_1)_m$ is H, F, Cl, $CH_3$ or CN, m is 1, $R_2$ is H or $CH_3$, n is 4, $(R_3)_p$ is H, F or $(C_1-C_4)$alkyl and p is 1, or a pharmacologically acceptable acid addition salt thereof.

3. A compound as claimed in claim 1, wherein $(R_1)_m$ is F, m is 1, $R_2$ is H, n is 4 and p is 0, or a pharmacologically acceptable acid addition salt thereof.

4. A method for preparing a compound having formula (I) as claimed in claim 1, comprising a) reacting a compound of the formula (II)

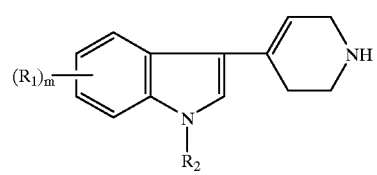

with a compound of the formula (III)

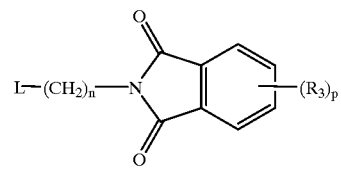

wherein L is a Leaving group, to yield the compound having formula (I);

or b) (i) reacting a compound of the formula (IV)

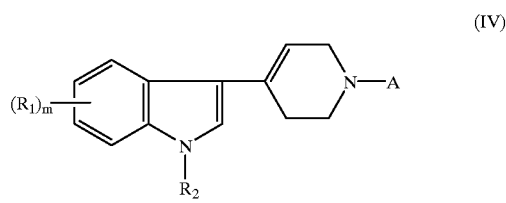

wherein A is a group $-(CH_2)_{n-1}-CN$, to reduce the compound of formula (IV) to yield an amine compound wherein A is a group $-(CH_2)_n-NH_2$, and (ii) reacting the amine compound with a phthalic anhydride compound of the formula (V)

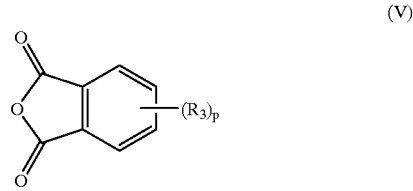

to yield the compound having formula (I), in which formulae $R_1$, m, $R_2$, n, $R_3$ and p have the meanings given in claim 1.

5. A pharmaceutical composition comprising at least one compound having formula (I) or a pharmacologically acceptable acid addition salt thereof as claimed in claim 1 or a mixture of the foregoing, and at least one pharmacologically acceptable auxiliary substance.

6. A method of preparing a composition as claimed in claim 5, comprising combining the at least one compound having formula (I) or the pharmacologically acceptable acid addition salt thereof, or the mixture of the foregoing, with the at least one pharmacologically acceptable auxiliary substance.

7. A method of treating a human or animal patient in need of treatment for at least one CNS disorder, comprising
   administering to the patient
   an effective dopamine $D_2$-receptor antagonizing amount, an effective serotonin reuptake inhibiting amount, or a combination of said amounts,
   of at least one compound having formula (I) or at least one pharmacologically acceptable acid addition salt thereof as claimed in claim 1, or a mixture of the foregoing.

* * * * *